(12) United States Patent  
Morris (10) Patent No.: US 10,376,651 B2  
(45) Date of Patent: Aug. 13, 2019

(54) INJECTION DEVICE

(71) Applicant: Sanofi, Paris (FR)

(72) Inventor: Anthony Paul Morris, Coventry (GB)

(73) Assignee: Sanofi, Paris (FR)

( * ) Notice: Subject to any disclaimer, the term of this patent is extended or adjusted under 35 U.S.C. 154(b) by 804 days.

(21) Appl. No.: 14/782,616

(22) PCT Filed: Apr. 8, 2014

(86) PCT No.: PCT/EP2014/056999  
§ 371 (c)(1),  
(2) Date: Oct. 6, 2015

(87) PCT Pub. No.: WO2014/166917  
PCT Pub. Date: Oct. 16, 2014

(65) Prior Publication Data  
US 2016/0067419 A1    Mar. 10, 2016

(30) Foreign Application Priority Data  
Apr. 10, 2013   (EP) .................................. 13163106

(51) Int. Cl.  
*A61M 5/20*       (2006.01)  
*A61M 5/31*       (2006.01)  
*A61M 5/315*      (2006.01)

(52) U.S. Cl.  
CPC .......... *A61M 5/31551* (2013.01); *A61M 5/20* (2013.01); *A61M 5/31528* (2013.01);  
(Continued)

(58) Field of Classification Search  
CPC .......... A61M 5/31551; A61M 5/31528; A61M 5/31553; A61M 5/31583; A61M 5/20;  
(Continued)

(56) References Cited

U.S. PATENT DOCUMENTS

2007/0021715 A1    1/2007   Kohlbrenner et al.  
2009/0054839 A1*   2/2009   Moller .............. A61M 5/14566  
                                                              604/135  
(Continued)

FOREIGN PATENT DOCUMENTS

CN       101184519       5/2008  
JP       2006-187629     7/2006  
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Lauren P Farrar  
(74) *Attorney, Agent, or Firm* — Fish & Richardson P.C.

(57) ABSTRACT

The invention refers to a handheld injection device comprising a housing (10, 20, 30), a piston rod (60), defining a first longitudinal axis (I) and located within the housing (10), a driver (70, 80, 90) coupled to the piston rod (60), a dose setting means (40), which is rotatable during dose setting, a power reservoir (100) for driving the driver (70, 80, 90), and a number wheel (130) for displaying a dose set by the dose setting means (40).

18 Claims, 3 Drawing Sheets (52) U.S. Cl.
CPC .... *A61M 5/31541* (2013.01); *A61M 5/31553* (2013.01); *A61M 5/31583* (2013.01); *A61M 5/3157* (2013.01); *A61M 2005/3126* (2013.01); *A61M 2205/581* (2013.01); *A61M 2205/582* (2013.01); *A61M 2205/583* (2013.01)

(58) Field of Classification Search
CPC ...... A61M 5/31541; A61M 2005/3126; A61M 5/3157; A61M 2205/582; A61M 2205/581; A61M 2205/583
See application file for complete search history.

(56) References Cited

U.S. PATENT DOCUMENTS

| | | | |
|---|---|---|---|
| 2009/0137964 A1 | 5/2009 | Enggaard et al. | |
| 2012/0157929 A1* | 6/2012 | Plumptre | A61M 5/31541 604/189 |
| 2012/0253287 A1* | 10/2012 | Giambattista | A61M 5/31553 604/189 |
| 2012/0283648 A1* | 11/2012 | Veasey | A61M 5/24 604/207 |
| 2012/0289908 A1* | 11/2012 | Kouyoumjian | A61M 5/31543 604/211 |

FOREIGN PATENT DOCUMENTS

| | | |
|---|---|---|
| JP | 2013-506447 | 2/2013 |
| WO | WO 2004/078241 | 9/2004 |
| WO | WO 2006/058883 | 6/2006 |
| WO | WO 2007/030857 | 3/2007 |
| WO | WO 2009/105910 | 9/2009 |
| WO | WO 2011/039207 | 4/2011 |
| WO | WO 2011/039208 | 4/2011 |
| WO | WO 2011/039229 | 4/2011 |
| WO | WO 2011/039233 | 4/2011 |

OTHER PUBLICATIONS

International Preliminary Report on Patentability in International Application No. PCT/EP2014/056999, dated Oct. 13, 2015, 5 pages.
International Search Report and Written Opinion in International Application No. PCT/EP2014/056999, dated Jun. 25, 2014, 8 pages.

* cited by examiner

INJECTION DEVICE

This application is a § 371 U.S. National Stage Application of PCT/EP2014/056999,filed Apr. 8, 2014, which claims priority to European Patent Application 1316106.1, filed Apr. 10, 2013, the entire contents of which are incorporated herein by reference The present invention is generally directed to a handheld injection device, i.e. a drug delivery device for selecting and dispensing a number of user variable doses of a medicament. Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. This known device is a manually driven device, where the component parts are in general disposed concentrically around a common longitudinal axis. During dose setting some component parts wind out of the housing and are pushed back into the housing during dose dispensing.

The device of WO 2004/078241 A1 comprises a last dose protection mechanism with a last dose nut, which is in threaded engagement with the driver and splined to the housing. Because the driver rotates relative to the housing during dose setting, the nut advances on the helical path defined by the thread on the driver. During dose dispensing the driver does not rotate, such that the nut maintains its position on the helical track. Thus, the position of the nut corresponds to the sum of the actually set dose and the already dispensed doses. A stop at the end of the helical track limits the maximum settable dose to the amount of medicament in the cartridge. Although the last dose protection mechanism of WO 2004/078241 A1 is reliable, a possible drawback may be that the user force is transmitted to the driver via a dose setting knob and the relatively long tubular driver, which may have a small degree of elasticity.

It is an object of the present invention to provide a drug delivery device with improved accuracy regarding the last dose mechanism. It is a further object to make the drug delivery device compact in size, preferably without components translating out of the housing during dose setting.

This object is solved by a device as defined in claim 1.

According to a first embodiment of the present invention the handheld injection device comprises a housing, a piston rod, a driver, a dose setting means, a power reservoir and a number wheel. The piston rod defines a first longitudinal axis and is located within the housing. The driver is coupled to the piston rod. The dose setting means comprises a dial grip, which is rotatable, preferably about a second longitudinal axis, at least during dose setting. The power reservoir drives the driver during dose dispensing. The number wheel is suitable for displaying a dose set by the dose setting means. To prevent an underdosage or a malfunction, the drug delivery device comprises a last dose protection mechanism for preventing the setting of a dose, which exceeds the amount of liquid left in a cartridge.

In a first alternative of this embodiment, the last dose protection mechanism comprises a nut member located interposed between the dial grip and the housing. In more detail, the dial grip may comprise a threaded section having an end stop, which is preferably located at the proximal end of the threaded section. Further, the housing comprises a splined section, with the last dose nut being interposed between and engaging threaded section of the dial grip and the splined section of housing.

In a second alternative of this embodiment, the dial grip is split into two components, namely a dial grip which is axially constrained to the housing and a dispense button, which is splined to the dial grip and axially displaceable by the user to dispense a dose. The dispense button preferably carries the splined features which engage with the housing to lock the dispense button and dial grip rotationally during dispense. For tis second alternative, the thread for the last dose nut could be on the dispense button. In other words, preferably the dial grip becomes the dispense button, and a separate dial grip is splined to the outside of the button and axially retained to the housing.

As the dial grip (or the dispense button if provided) preferably rotates relative to the housing during dose setting and is preferably rotationally constrained to the housing during dose dispensing, these two components are suitable to form a reliable and robust last dose limiter mechanism. Providing the last dose nut directly between the dial grip or dispense button, which is used to set a dose, and the stationary housing brings the advantage, that the last dose limitation does not involve further interposed components which may, even by a small degree of elasticity, negatively influence the accuracy of the last dose mechanism. The last dose nut may be a full nut or a part thereof, e.g. a half nut.

According to a preferred embodiment of the invention, driver, the dose setting means and the number wheel are coupled such that the angle of rotation of the number wheel differs from that of the dose setting means and driver for a single dose increment. In other words, there is a gear ratio between these components which allows improving the display and at the same time reducing the dimensions of the device.

This may be achieved by providing an epicyclic gearbox. The components of the device may form different elements of the epicyclic gearbox. For example, the driver may be the gearwheel and the number wheel may be the internal ring gear. Preferably, the driver comprises an internal ring gear, the number wheel comprises an external gearwheel and the dose setting means, preferably the dial grip, is rotationally constrained to a planet carrier having at least one planet gear, which meshes with the internal ring gear of the driver and the gearwheel of the number wheel. With the at least one planet gear interposed between the internal ring gear of the driver and the gearwheel of the number wheel an epicyclic gearbox is formed, which enables the angular resolution of different sections of the device, for example the driver, the planet carrier and the number wheel, which may carry a number marking from 0 to 9 on its outer cylindrical surface, to be varied and optimized to suit their functional requirements. In other words, during dialing, rotation of the driver may be prevented, thus creating a gear ratio between the planet carrier, which is for example splined to the dose setting means, and the number wheel. In this mode, rotation of the dose setting means causes the number display of the number wheel to move. During dispensing, rotation of the planet carrier may be prevented, thus creating a gear ratio between the driver and the number wheel. In this mode the dose setting means is preferably locked in rotation and rotation of the driver, under the action of the power reservoir, e.g. a motor spring, causes the number display of the number wheel to move. This results in a highly reliable and precise, and yet compact, display of the actually set dose of the injection device.

In a further development of this idea, the planet carrier comprises three bosses, each carrying a planet gear, which meshes with the internal ring gear of the driver and the gearwheel of the number wheel.

According to a second independent embodiment of the present invention the handheld injection device comprises a housing, a piston rod, a driver, a dose setting means, a power reservoir, a number wheel and an additional second number wheel for displaying a dose set by the dose setting means, wherein the second number wheel is coupled to the (first) number wheel such that a continuous rotation of the first number wheel is translated into an intermittent motion of the second number wheel. In some cases it might be useful for the display of a drug delivery device not to indicate a small rotation of the dosing element. This may occur if the display is not provided with numbers, symbols or the like for every dose increment the dosing element is rotated. In other words, the display may indicate only every ten dose units instead of every single dose unit. In such cases it might be desirable that the display is not in an intermediate position, e.g. between two numbers. Thus, a display member may be coupled to the dose setting means such that a continuous rotation of the dose setting means is translated into an intermittent motion of the display member. An example for a display member which is indirectly coupled to the dose setting means is a Geneva drive.

The transmission between the first and second number wheels preferably involves that the (first) number wheel comprises a single tooth or protrusion which engages with an index wheel having a set of gear teeth. Further, a cam interface of the number wheel may be provided constraining rotation of the index wheel when the gear teeth are not engaged. The second number wheel preferably interfaces with the index wheel via a set of meshing gear teeth.

According to a preferred embodiment, the injection device comprises a first number wheel which is coupled to the dose setting means by the epicyclic gear box and a second number wheel which is indirectly coupled to the dose setting means. Typically, one of these number wheels is used to display the single digits whereas the other number wheel is used to display the tens of a two-digit or a more-digit number. For example in this case, the second number wheel may be coupled to the dose setting means such that a continuous rotation of the dose setting means is translated into an intermittent motion of the second number wheel, and the first number wheel may be coupled to the dose setting means such that a continuous rotation of the dose setting means is translated (via the epicyclic gear box) into a continuous motion of the first number wheel. Thus, the first number wheel may be used to display the ones and the second number wheel may be used to display the tens. If the maximum selectable dose of a device is e.g. 120 units, the second number wheel comprises the numbers zero to twelve and the first number wheel comprises the numbers zero to nine.

The injection device may further comprise a release clutch, which is arranged such that it prevents rotation of the driver during dose setting and allows rotation of the driver during dose dispensing.

The first longitudinal axis is preferably parallel to and spaced from the second longitudinal axis, i.e. there is an offset between the two axes on which the component parts of the device are arranged. Due to some of the component parts being located next to others instead of the conventional concentrically arrangement, the cross-section of the device becomes rather elongated than the usual circular pen-shape. This improves handling of the device at least for some users. Further, the device may be made less bulky, which again improves handling.

Providing the power reservoir for driving the driver reduces the force required from the user during dose dispensing. This is especially helpful for users with impaired dexterity. The power reservoir may comprise a spring, which may be a preloaded (pre-charged) spring or a spring which has to be loaded by the user during dose setting. Preferably, the spring is pre-charged for the expected life of the device, i.e. such that a user is not required to re-charge or strain the spring at any time. Suitable spring types involve compression springs and torsion springs. According to a preferred embodiment of the invention, the spring is a reverse wound flat spiral spring, which is a wound up band-type spring which is wound up in its charged state counter to its unstressed winding direction. Preferably, a first end of the spring is attached to a first spool, which may be located on the first longitudinal axis, and a second end of the spring is attached to a second spool, which may be located on the second longitudinal axis. For driving the driver, one of the spools may be coupled to the driver, e.g. by means of a direct splined coupling. As an alternative, a releasable coupling may be used, e.g. a pair of teeth rings. As a further alternative, the spool may be an integral part of the driver.

The driver may comprise a tubular element which is coupled to the piston rod. Preferably, this tubular element at least partly surrounds the piston rod. The coupling may be a releasable coupling, however it is preferred that the driver is permanently coupled to the piston rod, e.g. via a splined interface or a threaded interface. A drive tube being a component part of the driver is preferably arranged rotatable about the first longitudinal axis and directly coupled to the piston rod.

The driver may further comprise at least one further component part, for example a drive sleeve or drive gear which is rotatable about the second longitudinal axis. Thus, two component parts of the driver may be arranged with an offset on parallel axes. Preferably, the component parts of the driver are permanently coupled to each other such that rotation of one component causes rotation of the other component. For example meshing pinions might be provided on each of the two driver components. The drive sleeve may be coupled to the power reservoir such that the power reservoir drives the driver components, e.g. via a splined interface. The drive sleeve or drive gear may comprise two or more component parts, which are rotationally constrained to each other, but which may allow relative axial displacement, preferably for performing a coupling or de-coupling function.

According to a further preferred embodiment, the dose setting means comprises a dial grip which is rotatable about the second longitudinal axis. Preferably, the dial grip is decoupled from the driver during dose setting and during dose dispensing. In other words, during dose setting, the dial grip does not rotationally entrain the driver, whereas during dose dispensing the driver does not rotationally entrain the dial grip. However, the dial grip entrains the driver axially as the user presses the button to move to a dispensing mode and the driver entrains the dial grip axially at the end of dispense, as the trigger button is released.

Initiating dose dispensing usually requires that a user presses a button or trigger, for example the proximal end of the dial grip. Preferably, at least one component part of the dose setting means and/or the driver is axially displaceable between a dose setting position, in which the dose setting means is rotatable relative to the housing and relative to the driver, and a dose dispensing position, in which the driver is rotatable relative to the housing. The axially displaceable dose setting means may be a dial grip which is used for dose setting. Preferably, the axially displaceable component travels along the second longitudinal axis between its dose setting position and its dose dispensing position.

The sequence of dose setting and dose dispensing usually requires a relative movement of some of the components either during dose setting and/or during dose dispensing. Various different embodiments of achieving this result are possible, some of which are described in the prior art mentioned above. There may be a clutch arranged between the driver and the number wheel, wherein the clutch allows relative rotation of the driver and the number wheel during dose setting and rotationally constrains the driver and the number wheel during dose dispensing. According to a preferred example of the invention, the injection device may further comprise a first clutch arranged between the driver and the housing (which is engaged during dialing, disengaged during delivery) and a second clutch between the dial grip and the housing (which is disengaged during dialing, engaged during delivery). The resulting action of the above two clutches may infer a releasable coupling between the driver and the number wheel. Accepting that there is a gear ratio between the driver and the number wheel, these components become rotationally constrained.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to avoid overdosage. Preferably, the limits for the minimum dose and the maximum dose are provided by hard stop features. In a preferred embodiment of the invention, such a maximum settable dose and a minimum settable dose limiter comprises a threaded section of the number wheel having end stops, and a splined section of the housing, with a dose nut (limiter) being interposed between and engaging threaded section of the number wheel and the splined section of housing. The end stops are preferably two end stops located on opposite (distal and proximal) positions of the threaded section. Thus, upon rotation of the number wheel relative to the housing during dose setting or dose dispensing, the dose nut, which is splined to the housing, travels on the threaded section between the respective maximum settable dose and a minimum settable dose stops. Abutment of the dose nut with one of these end stops limits the rotational movement of the number wheel and, thus, further dose setting or further dose dispensing. This creates a reliable and robust limiter mechanism. The dose nut may be a full nut or a part thereof, e.g. a half nut.

To prevent an underdosage or a malfunction, the drug delivery device may comprise a last dose protection mechanism for preventing the setting of a dose, which exceeds the amount of liquid left in a cartridge. For example, the last dose protection mechanism comprises a nut member located interposed between the dial grip and the housing. As the dial grip rotates relative to the housing during dose setting and is rotationally constrained (via splines) to the housing during dose dispensing, these two components are suitable to form a reliable and robust last dose limiter mechanism. In more detail, the dose setting means preferably comprises a dial grip, which is rotationally constrained to the planet carrier and which comprises a threaded section having an end stop, which is preferably located at the proximal end of the threaded section. Further, the housing may comprise a splined section, with a last dose nut being interposed between and engaging threaded section of the dial grip and the splined section of housing. Providing the last dose nut directly between the dial grip, which is used to set a dose, and the stationary housing brings the advantage, that the last dose limitation does not involve further interposed components which may, even by a small degree of elasticity, negatively influence the accuracy of the last dose mechanism. The last dose nut may be a full nut or a part thereof, e.g. a half nut.

If the piston rod is a threaded lead screw with the housing having a threaded portion cooperating with a threaded outer surface of the piston rod, rotation of the piston rod during dose dispensing results in an axial movement of the piston rod. As an alternative the piston rod may be in threaded engagement with the driver and be splined to the housing.

Preferably, the device further comprises at least one clicker producing an audible and/or tactile first feedback during dose setting and/or during dose dispensing. A clicker producing an audible and/or tactile feedback during dose setting and/or during dose correction (cancelling of a set dose without dispensing) may comprise a compliant clicker arm on the housing engaging teeth or the like on the dial grip. A further clicker producing an audible and/or tactile feedback during dose dispensing may comprise a further compliant clicker arm on the housing engaging teeth or the like on the driver, preferably a pinion coupling the drive tube to the drive gear.

To improve handling of the device, the length of the device before and after dose setting is preferably the same. In other words, there is no dial extension due to components winding out of the housing during dose setting. Preferably, the dose setting means and the driver are arranged in the housing such that they are prevented from axial displacement along one of the longitudinal axes during dose setting and during dose dispensing. However, an axial movement of at least some of the components between dose setting and dose dispensing may be possible for switching between a dose setting position and a dose dispensing position of the device.

The drug delivery device may comprise a cartridge containing a medicament. Further, a movable bung may be provided in the cartridge.

Usually, injection devices require a so called priming prior to the first use to close a possible gap between the cartridge bung and the piston rod and to overcome tolerances within the device. For the priming step, a user has to set a small dose and to dispense this dose while monitoring whether e.g. fluid leaves the device. This action has to be repeated until e.g. fluid actually leaves the device. According to a preferred embodiment, the piston rod comprises a bearing or tip at its end facing the bung, wherein in the unused delivery state of the device, the bearing abuts the bung. In other words, priming is no longer necessary. This prime elimination may be achieved in a device where the driver is coupled to the piston rod by rotating the driver during the assembly process until the piston rod is moved to a position abutting the cartridge bung. This position may be determined by an increase in the force or torque required to rotate the driver. As an alternative, the axial position of the piston rod relative to the housing may be sensed.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-GluGly-Thr-Phe-Thr-Ser-Asp-Leu-Ser-Lys-Gln-Met-Glu-Glu-Glu-Ala-Val-Arg-Leu-Phe-Ile-GluTrp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38 Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains.

These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The present invention provides a mechanism for use in a medical device that can be operated to deliver a number of user variable doses of medicament from a cartridge, via a needle. The device is disposable and is delivered to the user in a fully assembled condition ready for use.

The mechanism uses a motor spring to store energy. This is supplied to the user in a pre-charged state and no subsequent recharging is necessary for the entire life of the device. The user selects the required dose using an input dial and set dose display incorporated into the mechanism. The spring energy is stored until the device is triggered for dispense at which point a proportion of the energy stored is used to deliver the medicament from the cartridge to the user.

Any dose size can be selected between zero and a predefined maximum, in one unit increments. The mechanism permits cancelling of a dose without any medicament being dispensed, by rotation of the dose selection dial (dial grip) in the opposing direction to when selecting a dose.

The trigger (dial grip) is positioned towards the proximal end of the device and, on activation, dispenses medicament if the dose selected is greater than zero.

The device has low torque requirements to set a dose since the spring is pre-charged and low force requirements to trigger dispense of medicament. It has relatively low part count and is particularly attractive for cost sensitive device applications.

The mechanism has the added advantage that several key components are arranged in parallel driven by a gear arrangement. This reduces the overall length of the device.

The invention introduces an alternative number display system, which provides the numerical display of every dose position (existing devices typically display numerals at even dose positions only). Despite more numbers being displayed, the number marking size is comparable with existing devices.

The invention introduces a mechanism by which the angular resolution (number of units per revolution) of specific sections of the mechanism can be varied and optimized to suit the required functionality.

Non-limiting, exemplary embodiments of the invention will now be described with reference to the accompanying drawings, in which.

Figures 1, 2:
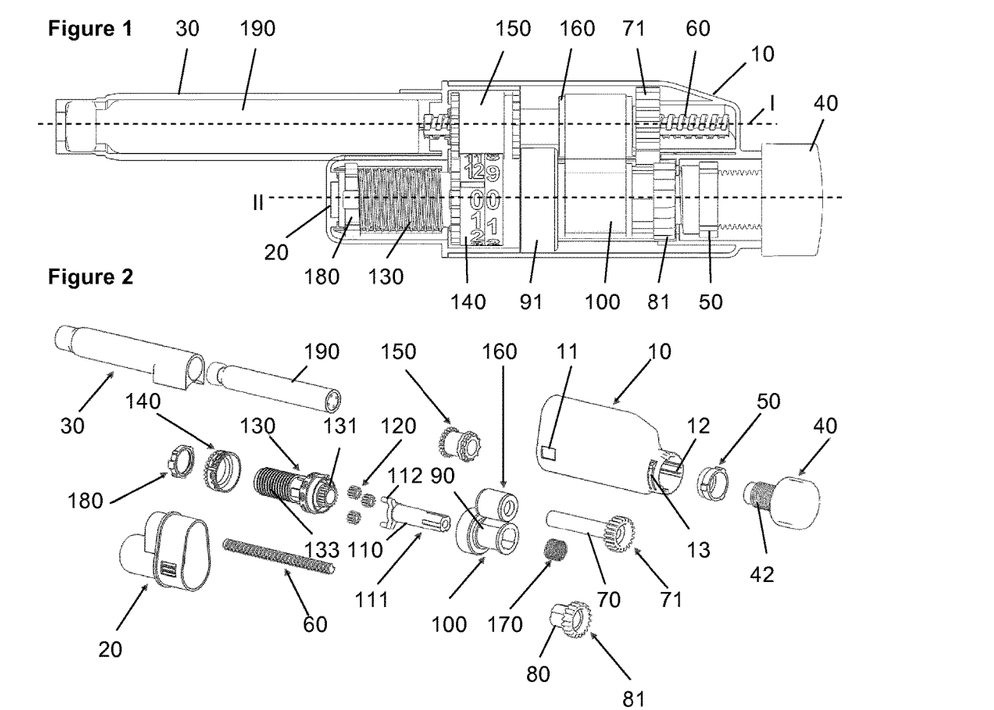
FIG. 1 shows a partly sectional view of an injection device in accordance with a first embodiment of the present invention.
FIG. 2 shows an exploded view of the components of the device of FIG. 1.
Figure 3:
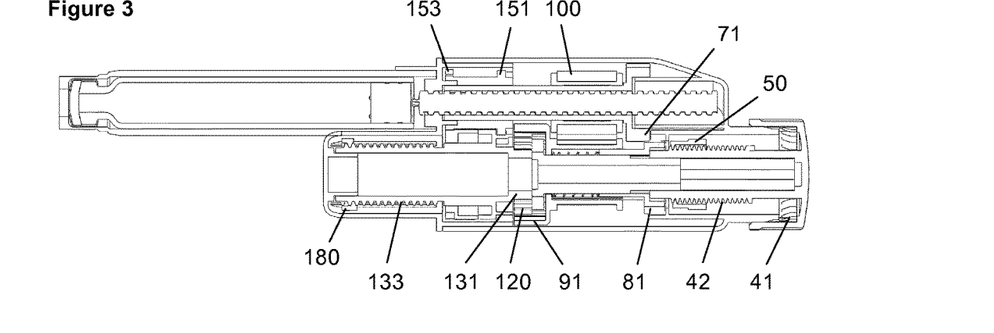
FIG. 3 shows a sectional view of the device of FIG. 1 in the dose setting state.
Figure 4A:
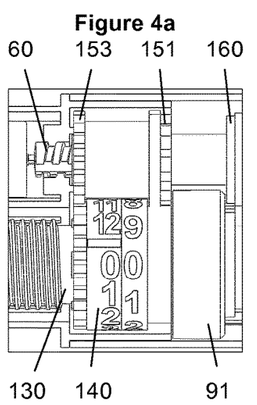
FIGS. 4a to 4c show different dose display states of the device of FIG. 1.
Figure 4B:
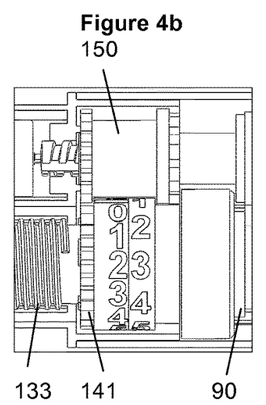
Figure 4C:
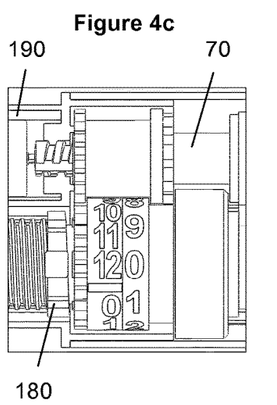
Figures 5A, 5B:
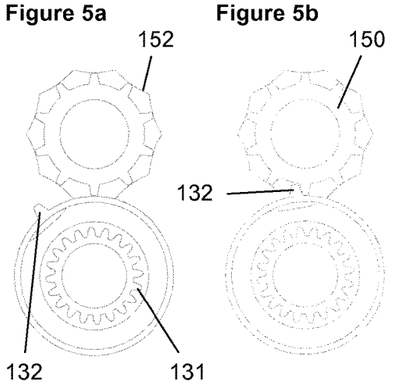
FIGS. 5a to 5d show different states of the index wheel advancement in the device of FIG. 1.
Figures 5C, 5D:
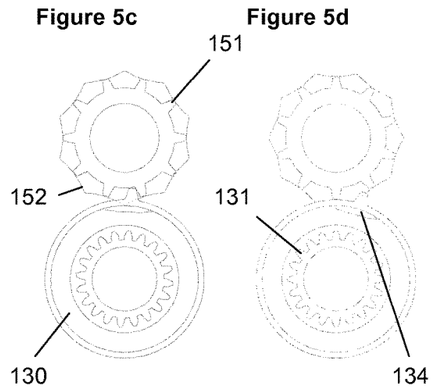

FIGS. 1 to 3 show a drug delivery device in the form of an injection pen. The device has a distal end (left end in FIG. 1) and a proximal end (right end in FIG. 1). The component parts of the drug delivery device are shown in FIG. 2. The drug delivery device comprises a main housing 10, a housing insert 20, a cartridge holder 30, a dial grip 40, a last dose nut 50, a piston rod 60 with a bearing (not shown), a drive tube 70, an upper drive sleeve part 80 and a lower drive sleeve part 90, a motor spring 100, a planet carrier 110, a set of three planet gears 120, a units gear 130, a tens wheel 140, an index wheel 150, a storage spool 160, a trigger spring 170, a dose nut 180 and a cartridge 190. Further, a cap (not shown in the Figures) may be provided. Thus, the mechanism consists of 19 unique components, excluding the liquid medicament cartridge 190. A needle arrangement (not shown) with a needle hub and a needle cover may be provided as additional components, which can be exchanged as explained above.

The components are located concentrically about either the principal, first axis I of the device (i.e. concentric with the medicament cartridge 190) or concentrically about a second axis II, parallel and offset to the first axis I of the device.

The main housing 10 is a generally tubular element with an oblong cross section with the lower side in FIG. 1 being widened compared with the upper side. A window 11 or aperture is provided in the main housing 10. The main housing 10, the body insert 20 and the cartridge holder 30 can be plugged or snapped together during assembly to close the main housing 10. Further, the housing components may be glued or welded together to form a rigid and permanently attached housing unit. The main housing 10 has a proximal aperture or socket in its lower region in FIG. 1, which is provided with internal splines 12 axially guiding and rotationally constraining last dose nut 50. Internal splines 12 or further internal splines may interact with the upper drive sleeve part 80 depending on its axial position within the housing 10. Further, a compliant clicker arm 13 interacting with dial grip 40 is provided on the socket surrounding the proximal aperture. An additional clicker arm (not shown in detail) is provided in the upper region of the main housing 10 (as seen in FIG. 1) for interaction with drive tube 70.

The dial grip 40 is located at the proximal end of the main housing 10. An internal ring of clicker teeth 41 engages with the compliant clicker arm 13 in the main housing 10 which provides detented orientation of the dial grip 40 during dialing. When depressed into its distal position (i.e. pushed to the left hand side compared with the position shown in FIG. 1), a splined interface engages with the main housing 10 to restrict rotation of the dial grip 40. The dial grip 40 creates an axial abutment with the upper drive sleeve part 80. Further, dial grip 40 comprises a section with an outer thread 42 having at least one rotational end stop. Last dose nut 50 is guided on this thread 42.

In an alternative embodiment (not shown in the Figures), the dial grip 40 is split into a dial grip component which does not move axially, and a dispense button component which is axially displaceable by a user to initiate dose dispensing. In this alternative embodiment the dispense button component has the thread for the last dose nut 50, and the splines which lock rotation of the dispense button component and dial grip component to the housing 10 during dispensing.

The last dose nut 50 has a threaded interface to the dial grip 40 and a splined interface to the main housing 10. It advances towards a rotational abutment with the dial grip 40 as a dose is dialled up by the user. This limits the maximum settable dose at the end of life of the cartridge.

The bearing 61 clips onto the end of the piston rod 60 and is able to rotate freely. The piston rod 60 is threaded to the housing insert 20 and has a splined interface to the drive tube 70.

The drive tube 70 is axially restrained within the main housing 10, and its gearwheel (pinion) 71 is permanently engaged with a corresponding gearwheel (pinion) 81 on the upper drive sleeve part 80.

The upper drive sleeve part 80 features the gearwheel 81 which creates a splined interface with the main housing 10, when the dial grip 40 is in its proximal position, which restricts its rotation. The upper drive sleeve part 80 is displaced axially by the dial grip 40 when the user depresses the dial grip 40. It has a splined interface with the lower drive sleeve part 90, thus rotationally constraining the upper and lower drive sleeve parts but allowing relative axial displacement.

The lower drive sleeve part 90 is axially restrained within the main housing 10. It features an internal ring gear 91, which engages with the planet gears 120. It provides an engagement with the spring material of the motor spring 100, and forms the drive spool of the motor spring 100 arrangement.

The motor spring 100 is located on a storage spool 160, which is assembled onto the drive tube 70 and is able to rotate freely. The motor spring 100 is charged during assembly by winding the spring material onto the lower drive sleeve part 90. In more detail, the power reservoir comprises a reverse wound flat spiral spring 100, that is a band-like spring, which has a spiral form in its unstressed condition and is wound counter to that unstressed spiral direction for tensioning the spring. A first end of the spring 100 is attached to a first spool 160, which is located on the first longitudinal axis I surrounding drive tube 70. A second end of the spring 100 is attached to a second spool, which is either located on the second longitudinal axis II and is rotationally constrained to the lower drive sleeve part 90 by splines and corresponding grooves inside the second spool or which is an integral part of the lower drive sleeve part 90. Spring 100 is fully charged (tensioned) during assembly of the device by winding the spring on the second spool (drive sleeve side), whereas the spring tends to wind back on the first spool 160. The power reservoir is dimensioned such that spring 100 is able to drive the piston rod 60 from its retracted position shown in FIGS. 1 and 3 to a position, where the cartridge bung is pushed in its most distal direction. In other words, recharging of the spring 100 is not necessary for emptying cartridge 190.

The planet carrier 110 has a splined interface 111 with the dial grip 40. It is axially restrained by the lower drive sleeve part 90 and the units gear 130. The planet carrier 110 features three cylindrical bosses 112 which provide rotational axes for the planet gears 120.

Figure 6:
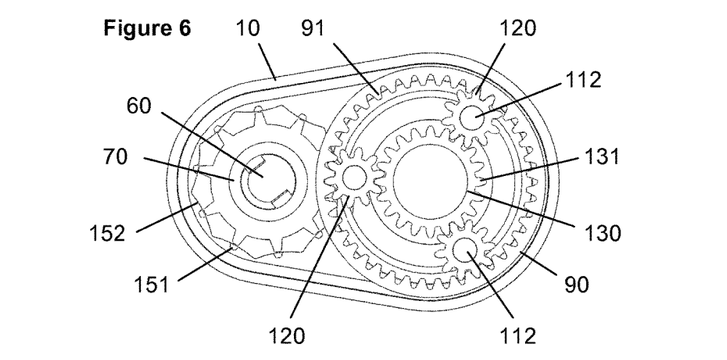
FIG. 6 shows an enlarged sectional view of a detail of the device of FIG. 1.

Although one single planet gear 120 would be sufficient for the function of the present invention, in the embodiment three planet gears 120 are shown located onto the planet carrier 110. The planet gears 120 are free to rotate about their local axes. As can be taken from FIG. 6, the planet gears 120 are interposed between the lower drive sleeve part 90 and the units gear 130 and mesh with respective gears thereof.

The units gear 130 features a gearwheel 131 which engages with the planet gears 120. Together with the ring gear 91 on the lower drive sleeve part 90, and the planet carrier 110 and planet gears 120, it forms an epicyclic gearbox. It carries number marking from 0 to 9 on its outer cylindrical surface. Further, it features a single tooth 132 which engages with the index wheel 150, once per revolution, to advance the dose display. The units gear 130 comprises an outer thread 133 interface and rotational abutments for the dose nut 180.

The tens wheel 140 is mounted concentrically to the units gear 130. It interfaces with the index wheel 150 via a set of meshing gear teeth 141 153, such that the tens wheel 140 rotates when the index wheel 150 rotates. It carries number markings from 0 to 12 on its outer cylindrical surface, which correspond to the second and third digit of the dose display. These number markings align with the number markings on the units gear 130 to create the numerical dose display.

The index wheel 150 is mounted concentrically to the drive tube 70. It interfaces with the units gear 130 via a set of gear teeth 151 on the index wheel 150, and the single tooth 132 on the units gear 130, such that the index wheel 150 is rotated one increment for each revolution of the units gear 130. As can be seen in FIGS. 5a to 5d, a cam interface 152 with the units gear 130 constrains rotation of the index wheel 150 when the gear teeth 132, 151 are not engaged. In the embodiment of FIGS. 2 and 4a to 4c the gear teeth 151 and the cam interface 152 interacting with the units gear 130 are located on the proximal side of the index wheel 150, whereas the gear teeth 153 interacting with the tens wheel 140 are located on the opposite distal side.

The trigger spring 170 is a compression spring, located between the lower drive sleeve part 90 and upper drive sleeve part 80. It acts to force the upper drive sleeve part 80 and dial grip 40 towards the proximal end of the device. The user overcomes the force of the trigger spring 170 when depressing the dial grip 40 to dispense a dose.

The dose nut 180 has a threaded interface to the units gear 130 and a splined interface to the housing insert 20. It translates, relative to the main housing 10, between rotational abutments with the units gear 130 which are generated at 0 units and maximum dose positions. The translation of the dose nut 180, relative to the main housing 10, facilitates visual analogue indication of the dose position of the device.

In the following, the function of the number display will be explained in more detail with reference to FIGS. 4a to 6. The interaction of the units gear 130, index wheel 150 and tens wheel 140 generates a counter display which enables every dose number to be displayed to the user. The number marking size is comparable to existing devices, which typically display even numbers only.

As the units gear 130 rotates, the dose display advances from 0 to 9. As rotation of the units gear 130 continues from 9 to 0, to complete one revolution, the single tooth 132 on the units gear engages with the gear teeth 151 on the index wheel 150, causing the index wheel 150 to rotate.

The cam profile 152 on the index wheel 150, which constrains rotation of the index wheel 150 when the units gear 130 is displaying digits 0 to 9, disengages from the units gear 130 as a recess 134 is provided in its cylindrical surface. As the index wheel 150 rotates one tooth increment the cam profile 152 reengages, constraining the index wheel 150 in its new orientation. The index wheel 150 is advanced by the units gear 130 as the units gear 130 rotates in either direction between the 9 and 0 digit position.

Via a geared interface 141, 153, the tens wheel 140 is rotated one increment when the index wheel 150 rotates one increment. Rotation of the tens wheel 140 causes the 2nd and 3rd digits of the dose display to advance by one position for each revolution of the units gear 130.

The counter type display requires angular resolution of 10 units per revolution on the units gear 130. Typically in existing devices, all rotating elements have the same angular resolution, implying that the dial grip 40, last dose nut 50 and piston rod 60 would also have angular resolution of 10 units per revolution. Existing devices using number display sleeves have angular resolution of 20 or 24 units per revolution. Therefore a 10 units per revolution device would require significant additional rotations of the dial grip 40 by the user to dial a dose which is likely to be inconvenient. It would require a significant number of additional revolutions of a last dose nut 50, which could impact on device length. It would also require a very fine pitch on the piston rod 60, which may impact the strength of the thread interface and the moulding feasibility of this component. Thus, providing a geared mechanism as explained below in more detail has significant advantages in combination with such a display mechanism.

The interaction of the lower drive sleeve part 90, planet carrier 110 and planet gears 120, and the units gear 130 generate an epicyclic gearbox which enables the angular resolution of different sections to be varied and optimised to suit their functional requirements. The axial motion of the dial grip 40 during dispensing causes splined interfaces to engage and disengage which changes the mode of the epicyclic gearbox.

During dialing, rotation of the lower drive sleeve part 90 is prevented by the splined interface between the upper drive sleeve part 80 and the main housing 10. A gear ratio therefore exists between the planet carrier 110, which is splined to the dial grip 40, and the units gear 130. In this mode, rotation of the dial grip 40 causes the number display to move.

During dispensing, rotation of the planet carrier 110 is prevented by the splined interface between the dial grip 40 and the main housing 10 and rotation of the lower drive sleeve is enabled by the disengagement of the splined interface between the upper drive sleeve part 80 and the main housing 10. A gear ratio therefore exists between the lower drive sleeve part 90 and the units gear 130. In this mode the dial grip 40 is locked in rotation and rotation of the drive gear (i.e. upper and lower drive sleeve parts 80, 90), under the action of the motor spring 100, causes the number display to move.

The angular resolution of the units gear 130 is set at 10 units per revolution to facilitate the counter display with every number shown. As an alternative, 20 units per revolution could be shown if even numbers only were shown (which negates the benefit of the gear ratios). The number of gear teeth on the lower drive sleeve part 90, planet gears 120 and units gear 130 are selected so that the angular resolution of the dial grip 40 during dialing, and the drive gear 80, 90 during dispensing generates an integer number of units per revolution. In this embodiment, the dial grip 40 has an angular resolution of 30 units per revolution and the drive gear 80, 90 has an angular resolution of 20 units per revolution.

Ensuring the gear ratios deliver an integer number of units per revolution is required to facilitate spline interfaces which advance by a single spline tooth for each unit increment of the device. During dialing, the dial grip's angular resolution of 30 units per revolution is similar to existing devices, so that a similar number of turns of the dial grip 40 is required to set a dose. The last dose nut 50, which interfaces with the dial grip 40 and the main housing 10 has the same angular resolution, and therefore the number of turns required is significantly reduced compared to a 10 units per revolution device, reducing the space required to package the last dose nut 50 feature.

During dispensing, the drive gear's angular resolution of 20 units per revolution allows the pitch of the piston rod 60 to be doubled, compared to a 10 units per revolution device. This generates a stronger piston rod 60 threadform, which is easier to mould.

In the following, the functioning of the disposable drug delivery device and its components will be explained in more detail.

Rotation of the dial grip 40 causes the planet carrier 110 and, thus, via the epicyclic gear boxes also the units gear 130 to rotate. Rotation of dial grip 40 relative to housing 10 generates a click sound by the interaction of compliant arm 13 and teeth 41. Trigger spring 170 pushes the upper drive sleeve part 80 together with dial grip 40 in the proximal dose setting position as shown in FIGS. 1 and 3. Thus, pinion 81 engages splines in the main housing 10, which rotationally constrains the drive gear 80, 90 with the motor spring 100 and the drive tube 70 to the main housing 10. In other words, the epicyclic gear box is in its dose setting mode, such that rotation of the planet carrier 110 relative to the stationary lower drive sleeve part 90 causes rotation of the units gear 130 via planet gears 120. The units gear 130 drives the tens wheel 140 via index wheel 150 as explained above, such that the actually set dose is visible through window 11 in main housing 10.

In the at rest position shown in FIGS. 1 and 3, the dose nut 180 is in its distal end position abutting the 0 U end stop at the distal end of thread 133, while due to the rotation of units gear 130 relative to the stationary housing insert 120, to which the dose nut 180 is splined, the dose nut 180 travels in the proximal direction towards its 120 U end stop at the proximal end of thread 133. If the dose nut 180 abuts its 120 U end stop, further rotation in the dose setting direction is prevented as the units gear 130 is blocked relative to the housing by dose nut 180. This limits the maximum settable dose.

Further, rotation of the dial grip 40 relative to the stationary main housing 10 causes an advancement of the last dose nut 50 on its helical path 42. FIGS. 1 and 3 show the last dose nut 50 in its most distal position which corresponds to a full cartridge 190. As can be seen from FIGS. 1 and 3, the pitch of thread 133 of dose nut 180 and thread 42 of last dose nut 50 are different, such that last dose nut 50 travels in the proximal direction more slowly. In other words, when using a full cartridge 190 dose nut 180 will abut its proximal 120 U end stop while last dose nut 50 has advanced only for a small distance on its track 42. On the other hand, if the cartridge 190 is nearly empty, i.e. the last dose nut 50 is near its proximal end stop, further rotation of the dial grip 40 in the dose setting direction may be prevented by the last dose nut 50 abutting its end stop, which blocks the dial grip 40 relative to main housing 10 via last dose nut 50.

Correction of a set dose is possible without dispensing medicament from cartridge 190 by rotating dial grip 40 in the opposite direction, while still being in its proximal dose setting position. This causes the number display 130, 140 to dial back toward 0 U and the dose nut 180 and the last dose nut 50 to travel back in the distal direction.

To dispense a dose, the dial grip 40 is pressed by the user against the force of trigger spring 170. It then engages with splines within main housing 10 rotationally constraining the dial grip and the housing. Further, dial grip 40 which acts on upper drive sleeve part 80 entrains the same in the distal direction disengaging the upper drive sleeve part 80 from the main housing 10. The device and its epicyclic gear box are now in its dose dispensing mode.

As motor spring 100 permanently acts on drive gear 80, 90, decoupling the drive gear from the housing results in a rotation of the drive gear 80, 90 relative to the housing. As the drive gear 80, 90 is permanently coupled to the drive tube 70 via pinions 71 and 81, drive tube 70 is rotated, too, which rotates piston rod 60. Due to its threaded engagement with housing insert 20, piston rod 60 is advanced in the distal direction acting via bearing 61 on the cartridge 190 bung, thus expelling medicament from the cartridge. The (not shown) clicker arm of main housing 10, which engages pinion 71 generates a dispense click.

In its dose dispensing mode with the planet carrier 110 being rotationally constrained to the main housing 10 via dial grip 40, the epicyclic gear box rotates units gear 130 via planet gears 120 in a direction opposite to the dose setting direction. In other words, the units gear 130 and the tens wheel 140 are rotated back to the 0 U position.

Together with the units gear 130 rotation, dose nut 180 is advanced back on its helical track 133 until it hits the distal 0 U end stop, which prevents further rotation of the units gear 130 and, thus, via the epicyclic gear box further rotation of the drive gear 80, 90 and the drive tube 70 with the piston rod 60.

As the dial grip 40 is rotationally constrained to the main housing 10, the last dose nut 50 does not move during dose dispensing. Thus, it maintains its position on the helical track 42, such that this position always corresponds to the sum of the actually set dose and the already dispensed doses.

Dose dispensing may be stopped at any time during dose dispensing by releasing dial grip 40. Trigger spring 170 then pushes upper drive sleeve part 80, which entrains dial grip 40, back in the proximal dose setting position. This reengages pinion 81 with the main housing 10, thus stopping further rotation caused by the motor spring 100. In the same way, the mechanism is brought back into its dose setting mode by releasing dial grip 40 after a dose has been fully dispensed, i.e. when dose nut 180 abuts its distal 0 U end stop.

Although not depicted in the present embodiment, the dose nut 180 and/or the last dose nut 50 may be used as additional display members, roughly indicating the actually set dose by the position of the dose nut 180 or roughly indicating the remaining contents of the cartridge 190 by the position of the last dose nut 50. This may be achieved by providing an additional window for the dose nut 180 in insert 20 or an additional window for last dose nut 50 in main housing 10.

Such a modified embodiment is depicted in FIGS. 7a to 8c. The component parts and their functions are mainly identical with the above first embodiment. However, the dose nut is modified in that it comprises a gauge surface 181 and in that the housing has an additional aperture 21 or window.

Figure 7A:
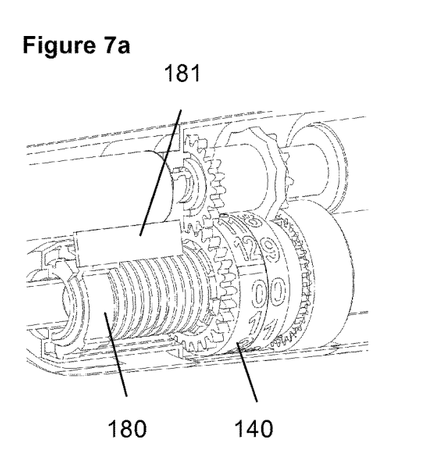
FIGS. 7a to 7c show in a cut open view different dose display states of a device of a further embodiment.
Figure 7B:
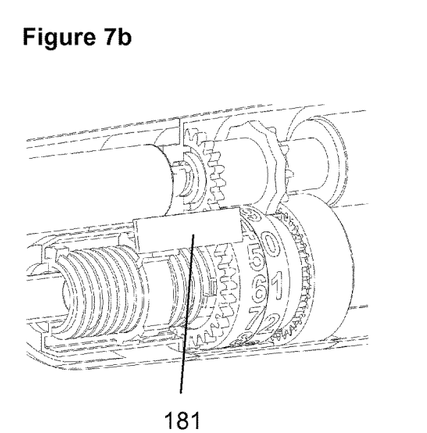
Figure 7C:
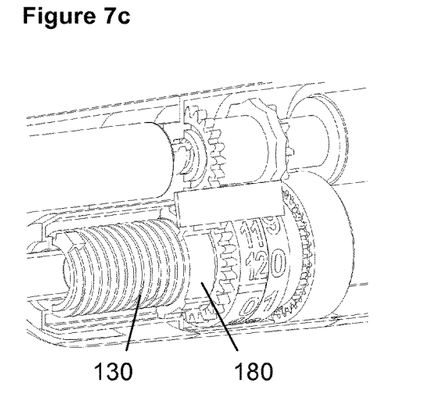
Figure 8A:
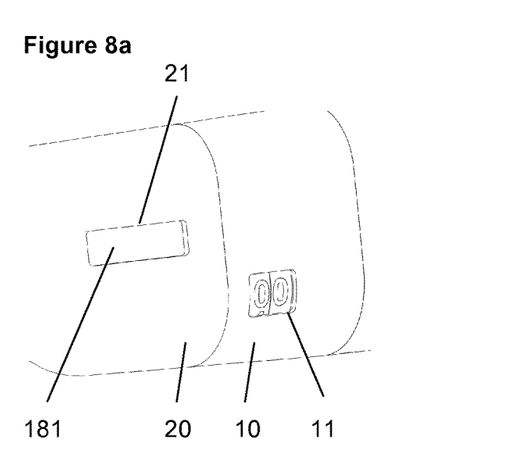
FIGS. 8a to 8c show in a side view different dose display states of the device of FIGS. 7a to 7c.
Figure 8B:
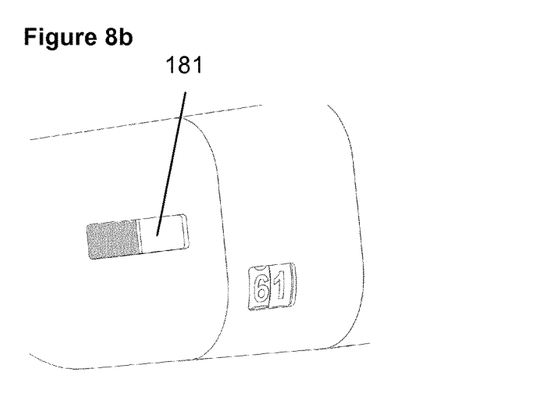
Figure 8C:
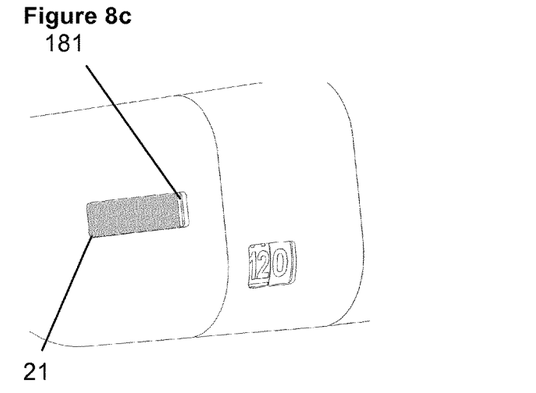

As mentioned above, the translation of the dose nut 180 relative to the housing 10, can provide additional analogue visual indication, referred to as an analogue gauge, of the dose position of the device. The additional aperture 21 is provided in the housing insert 20 and reveals the surface 181 of the dose nut 180 which translates axially in proportion to the dialled dose size. Translation of the surface 181 of the dose nut 180 reveals a further surface, which is formed by part of the main housing 10, housing insert 20 or the cartridge holder 30, which may be coloured to indicate a medicament type, or printed or marked to indicate particular dose amounts. FIGS. 7a and 8a show the device in a position with 0 units dialled, where the surface 181 is fully visible in the aperture 21. In FIGS. 7b and 8b a dose of 62 units is dialled such that only a portion of surface 181 is visible in aperture 21. The maximum dose of 120 units for this embodiment is dialled in FIGS. 7c and 8c where only a very small portion of surface 181 is visible in aperture 21.

This analogue gauge is beneficial for communicating the dose position of the device, or the rate of change of the dose position of the device, i.e. the dispense rate, during dispense of a dose. It is particularly beneficial for a device which may have a high dispense rate, where the existing numerical number display may be changing too quickly to be legible.

The invention claimed is:

1. A handheld spring-driven injection device comprising:
   a housing;
   a piston rod defining a first longitudinal axis, the piston rod being located within the housing;
   a driver coupled to the piston rod;
   a dose setting assembly which is rotatable during dose setting;
   a power reservoir for driving the driver, wherein the power reservoir is a motor spring of the handheld spring-driven injection device, the motor spring being dimensioned such that the motor spring can drive the piston rod from a retracted position into a distal position; and
   a number wheel for displaying a dose set by the dose setting assembly,
   wherein the dose setting assembly comprises a dial grip, which comprises a threaded section having an end stop, and wherein the housing comprises a splined section, with a last dose nut being interposed between and engaging the threaded section of the dial grip and the splined section of the housing,
   wherein the motor spring has a first end attached to a first spool, which is located on the first longitudinal axis, and a second end attached to a second spool, which is located on a second longitudinal axis, with one of the first and second spools being coupled to the driver.

2. The handheld spring-driven injection device according to claim 1, wherein the driver comprises an internal ring gear, the number wheel comprises a gearwheel and the dial grip is rotationally constrained to a planet carrier having at least one planet gear, which meshes with the internal ring gear of the driver and the gearwheel of the number wheel.

3. The handheld spring-driven injection device according to claim 2, wherein the planet carrier comprises three bosses, each carrying a planet gear, which meshes with the internal ring gear of the driver and the gearwheel of the number wheel.

4. The handheld spring-driven injection device according to claim 2, further comprising an additional number wheel for displaying the dose set by the dose setting assembly, wherein the additional number wheel is coupled to the number wheel such that a continuous rotation of the number wheel is translated into an intermittent motion of the additional number wheel.

5. The handheld spring-driven injection device according to claim 4, wherein the number wheel comprises a single tooth which engages with an index wheel having a set of gear teeth, with a cam interface with the number wheel constraining rotation of the index wheel when the set of the gear teeth are not engaged, and wherein the additional number wheel interfaces with the index wheel via a set of meshing gear teeth.

6. The handheld spring-driven injection device according to claim 1, further comprising a release clutch preventing rotation of the driver during the dose setting and allowing rotation of the driver during dose dispensing.

7. The handheld spring-driven injection device according to claim 1, wherein the dose setting assembly is rotatable about the second longitudinal axis during the dose setting, with the first longitudinal axis being parallel to and spaced from the second longitudinal axis.

8. The handheld spring-driven injection device according to claim 1, wherein the motor spring is a reverse wound flat spiral spring.

9. The handheld spring-driven injection device according to claim 8, wherein the driver comprises a drive tube which is rotatable about the first longitudinal axis and is directly coupled to the piston rod and a drive gear which is rotatable about the second longitudinal axis and is coupled to the power reservoir.

10. The handheld spring-driven injection device according to claim 7, wherein at least one component part of the dose setting assembly or the driver is axially displaceable along the second longitudinal axis between a dose setting position, in which the dose setting assembly is rotatable relative to the housing and relative to the driver, and a dose dispensing position, in which the driver is rotatable relative to the housing.

11. The handheld spring-driven injection device according to claim 1, wherein the number wheel comprises a threaded section having end stops, and wherein the housing comprises a further splined section, with a dose nut being interposed between and engaging threaded section of the number wheel and the further splined section of the housing.

12. The handheld spring-driven injection device according to claim 1, wherein the piston rod is a threaded lead screw and wherein the housing has a threaded portion cooperating with a threaded outer surface of the piston rod so that rotation of the piston rod results in an axial movement of the piston rod.

13. The handheld spring-driven injection device according to claim 1, further comprising at least one clicker producing an audible or tactile first feedback during the dose setting or during dose dispensing.

14. The handheld spring-driven injection device according to claim 1, wherein a length of the handheld spring-driven injection device before and after dose setting is the same.

15. The handheld spring-driven injection device according to claim 1 further comprising a cartridge containing a medicament.

16. The handheld spring-driven injection device according to claim 1, wherein the dial grip comprises an axially displaceable dispense button, the dispense button comprising a thread for the last dose nut, wherein the splined section of the housing locks rotation of the dispense button during dose dispensing.

17. A handheld spring-driven injection device comprising:
a housing;
a piston rod defining a first longitudinal axis, the piston being located within the housing;
a driver coupled to the piston rod;
a dose setting assembly which is rotatable during dose setting;
a power reservoir for driving the driver, wherein the power reservoir is a motor spring of the handheld spring-driven injection device, the motor spring being dimensioned such that the motor spring can drive the piston rod from a retracted position into a distal position; and
a number wheel for displaying a dose set by the dose setting assembly,
wherein the dose setting assembly comprises a dispense button, which comprises a threaded section having an end stop, and wherein the housing comprises a splined section, with a last dose nut being interposed between and engaging the threaded section of the dispense button and the splined section of the housing,
wherein the motor spring has a first end attached to a first spool, which is located on the first longitudinal axis, and a second end attached to a second spool, which is located on a second longitudinal axis, with one of the first and second spools being coupled to the driver.

18. The handheld spring-driven device of claim 17, wherein the dose setting assembly further comprises a dial grip splined to an outside of the dispense button and axially retained to the housing.

* * * * *

UNITED STATES PATENT AND TRADEMARK OFFICE
CERTIFICATE OF CORRECTION

PATENT NO. : 10,376,651 B2
APPLICATION NO. : 14/782616
DATED : August 13, 2019
INVENTOR(S) : Anthony Paul Morris It is certified that error appears in the above-identified patent and that said Letters Patent is hereby corrected as shown below:

In the Specification

Column 1, Line 5, delete "1316106.1," and insert -- 13163106.1, --.

Column 1, Line 7, delete "reference" and insert -- reference. --.

Signed and Sealed this
Twenty-fourth Day of December, 2019

Andrei Iancu
*Director of the United States Patent and Trademark Office*